United States Patent [19]

Schreiber et al.

[11] Patent Number: 4,617,145
[45] Date of Patent: Oct. 14, 1986

[54] 1-METHYL-2(2-METHYLBUTYL) CYCLOHEXANOL DERIVATIVES AND ORGANOLEPTIC USES THEREOF

[75] Inventors: William L. Schreiber, Jackson; Anubhav P. S. Narula; Marie R. Hanna, both of Hazlet, all of N.J.

[73] Assignee: International Flavors & Fragrances Inc., New York, N.Y.

[21] Appl. No.: 800,429

[22] Filed: Nov. 21, 1985

[51] Int. Cl.[4] .......................... A61K 7/46; C11B 9/00
[52] U.S. Cl. ................................ 252/522 R; 560/231; 568/832; 568/833; 568/834
[58] Field of Search ..................... 252/522 R; 568/832, 568/833, 834; 560/231

[56] References Cited

U.S. PATENT DOCUMENTS 4,277,618  7/1981  Helmlinger et al. ............... 560/231
4,378,428  3/1983  Helmlinger et al. ............ 252/522 R

FOREIGN PATENT DOCUMENTS 1411785  10/1975  United Kingdom ............ 252/522 R

OTHER PUBLICATIONS

Arctander "Perfume and Flavor Chemistry", published by author, (1969), Montclair, NJ, (U.S.A.).

Primary Examiner—Werren B. Lone
Attorney, Agent, or Firm—Arthur L. Liberman

[57] ABSTRACT

Described are the 1-methyl-2(2-methylbutyl) cyclohexanol derivatives defined according to the generic structure:

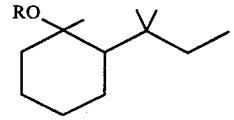

wherein R represents hydrogen, MgCl, MgBr, lithium or acetyl; and uses of such 1-methyl-2(2-methylbutyl) cyclohexanol derivatives where R is hydrogen or acetyl for their organoleptic properties in augmenting or enhancing the aroma of perfume compositions, colognes or perfumed articles. Also described is the process for preparing such 1-methyl-2(2-methylbutyl) cyclohexanol derivatives including the reactions:

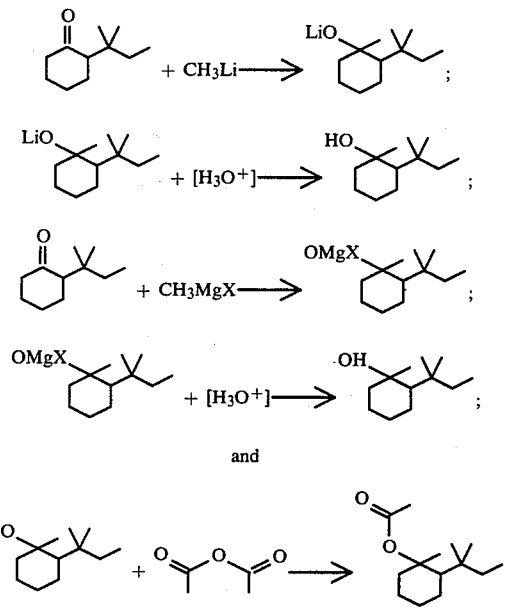

wherein the latter reaction takes place using a methane sulfonic acid catalyst.

14 Claims, 9 Drawing Figures

GLC PROFILE FOR BULKED FRACTIONS 1-3 OF EXAMPLE I.

GLC PROFILE FOR EXAMPLE I. CRUDE

GLC PROFILE FOR FRACTION I OF EXAMPLE II.

GLC PROFILE FOR EXAMPLE II. CRUDE

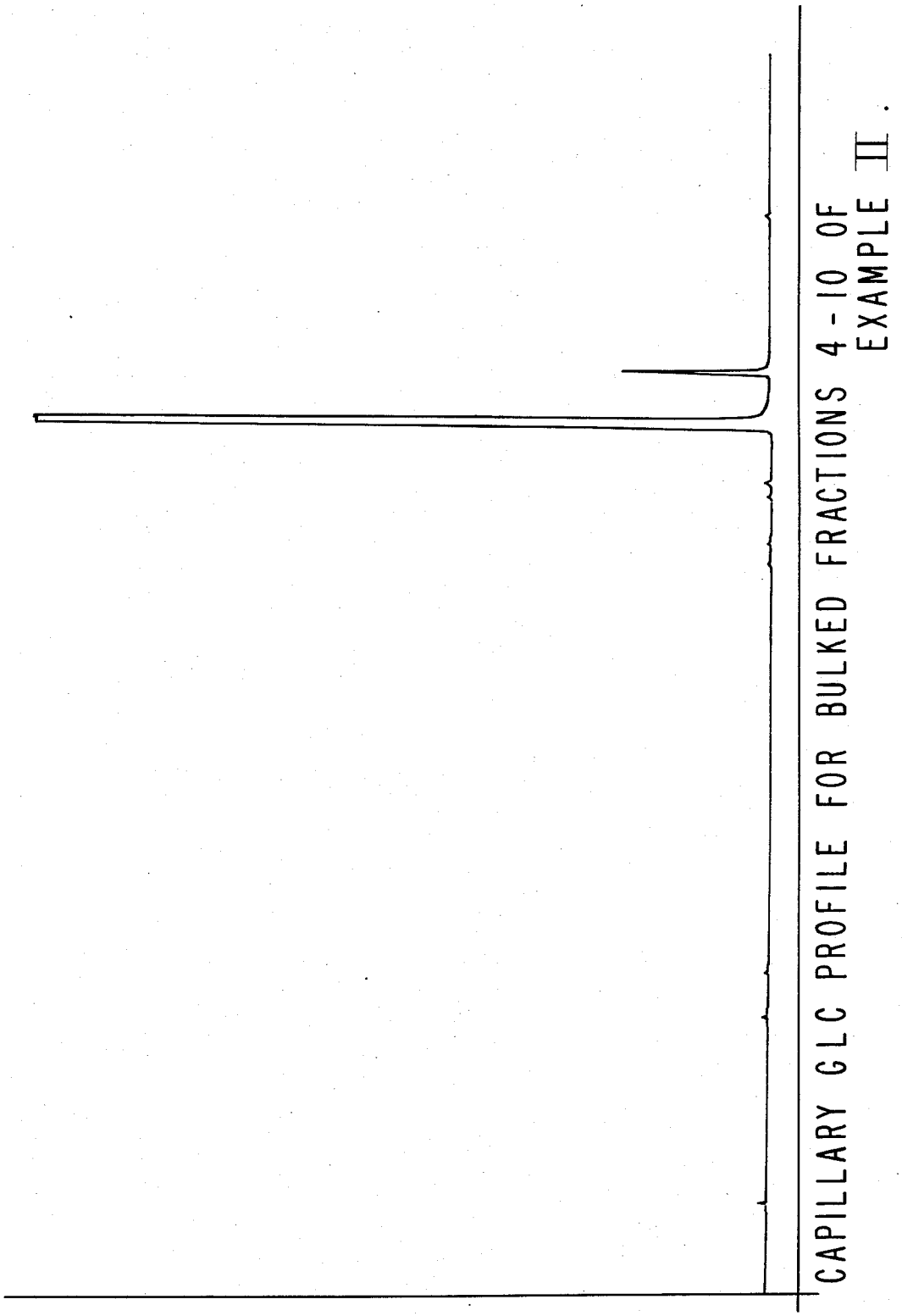
FIG.6 CAPILLARY GLC PROFILE FOR BULKED FRACTIONS 4-10 OF EXAMPLE II.

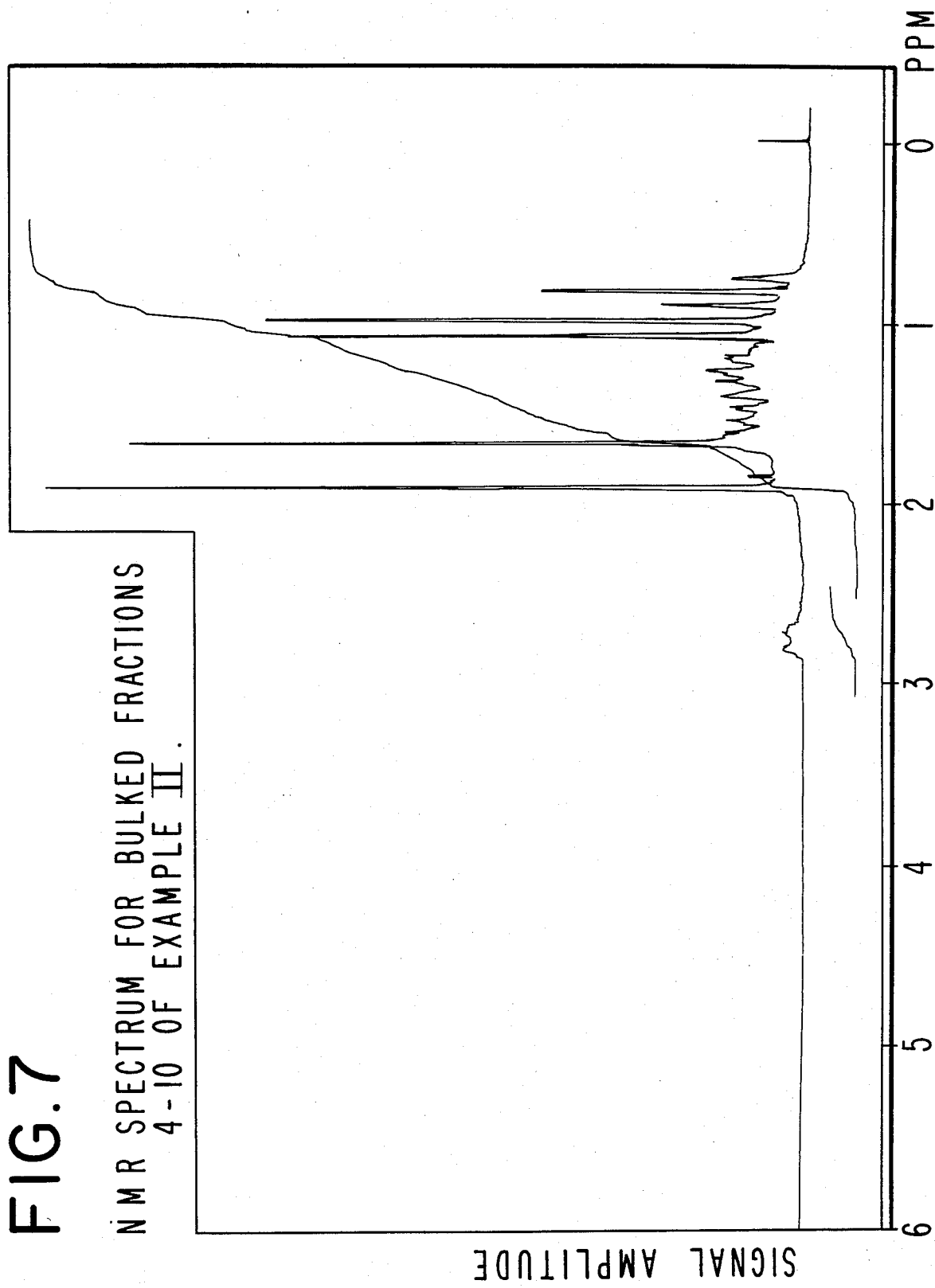
FIG. 7 NMR SPECTRUM FOR BULKED FRACTIONS 4-10 OF EXAMPLE II.

1-METHYL-2(2-METHYLBUTYL) CYCLOHEXANOL DERIVATIVES AND ORGANOLEPTIC USES THEREOF

BACKGROUND OF THE INVENTION

This invention relates to 1-methyl-2(2-methylbutyl)-cyclohexanol derivatives defined according to the generic structure:

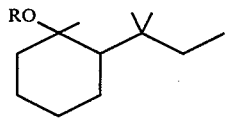

wherein R represents acetyl, hydrogen, MgCl, MgBr or lithium and uses of the compounds having the structures:

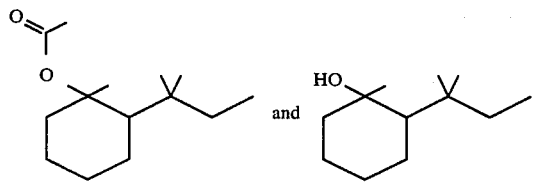

(where R represents hydrogen or acetyl) for their organoleptic properties in augmenting or enhancing the aroma of perfume compositions, colognes or perfumed articles including solid or liquid anionic, cationic, nonionic or zwitterionic detergents, fabric softener compositions, fabric softener articles, cosmetic powders, hair preparations and the like.

There is a continuing search for materials having desirable fragrance in organoleptic properties. Such materials are sought either to replace costly natural materials or to provide new fragrances of perfume types which have not heretofore been available.

Especially desirable qualities for substances having interesting fragrances are stability in a wide variety of perfumed articles and perfume compositions, ease of manufacture, intensity and pleasantness of aroma.

Particularly desirable in the perfume, cologne and perfumed article area are fragrance nuances which can be described as earthy, minty, camphoraceous, woody, ambery and herbaceous with floral and cedarwood undertones and cooling effects.

Tertiary alkyl cyclohexanol derivatives have been previously described in perfumery.

Thus, U.S. Pat. Nos. 4,277,618 issued on July 7, 1981 and 4,375,428 issued on Mar. 3, 1983 (Helmlinger, et al) described the genus of compounds defined according to the structure:

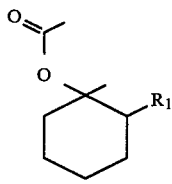

useful for their organoleptic properties, particularly in perfumery, wherein $R_1$ represents secondary butyl, tertiary buryl or cyclohexyl. Specifically, at column 5 lines 42–43 the compound having the structure:

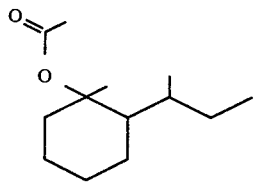

is described as having an amber and woody aroma suggesting animal warmth and tobacco-like. The compound having the structure:

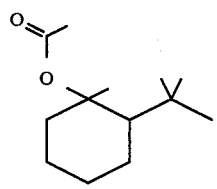

is described at column 6 lines 19 and 20 as having an "amber-like, woody, cedar-like, patchouli and vetiver aroma".

U.K. Pat. No. 1,411,785 filed on Apr. 5, 1973 and published on Oct. 29, 1975 discloses the compound having the structure:

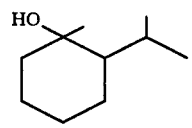

as having a minty aroma and the compound having the structure:

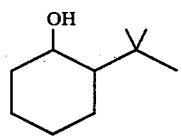

as having an earthy-mint aroma. New case specification 1,411,785 discloses the genus of compounds having the structure:

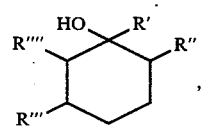

broadly having a "cooling effect on skin", where R'—R'''' represents hydrogen or $C_1$–$C_5$ alkyl and the sum of the carbon atoms in R'—R'''' is 3–7.

Arctander, "Perfume and Flavor Chemicals (Aroma Chemicals)" Volume 1 published in 1969 discloses for use in perfumery at monograph 167 the compound having the structure:

at monograph 438 the compound having the structure:

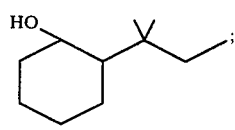

at monograph 432 the compound having the structure:

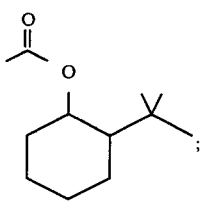

and at monograph 167 the compound having the structure:

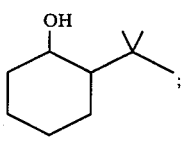

At monograph 167 it is indicated that the compound having the structure:

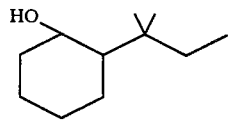

is used as an intermediate in preparing the compound having the structure:

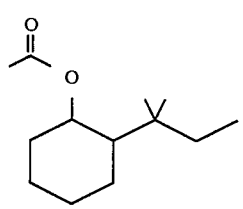

and that the compound having the structure:

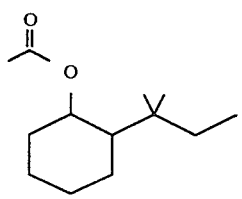

has a "camphoraceous, balsamic-green and somewhat sweet odor reminiscent of certain pine needle oils. It is further stated that "its woody undertones make it compatible with patchouli oil making the overall odor drier". Arctander further states that the compound having the structure:

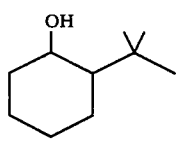

(at monograph 432) has a "powerful, camphoraceous, piney, mostly minty and somewhat tarry odor of great tenacity. " Arctander further states that the compound having the structure:

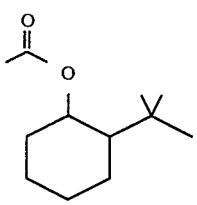

at monograph 438 has a "piney-woody, fruity, powerful and fresher odor with a slightly green undertone."

The compounds defined according to the structure:

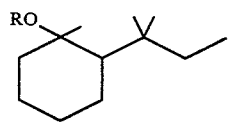

of our invention have unexpected, unobvious and advantageous properties insofar as their perfumery properties are concerned over the compounds of the prior art; insofar as their quality, tenacity and strengths are concerned.

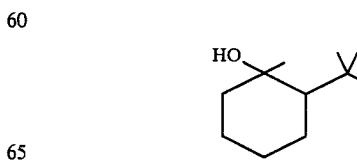

(Conditions: Carbowax column programmed at 150°–200° C. at 8° C. per minute).

Figure 2:
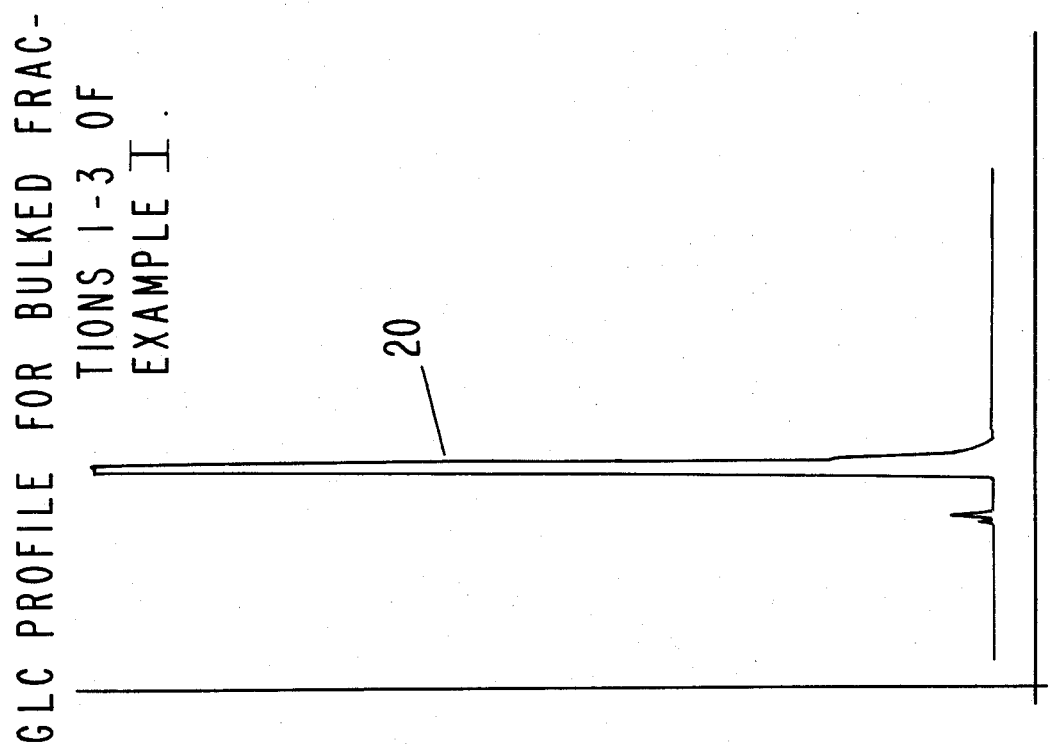

FIG. 2 is the GLC profile for bulked distillation fractions 1-3 of the distillation of the reaction product of Example I containing the compound having the structure:

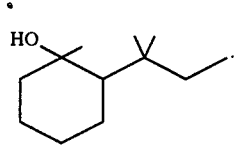

Figure 3:
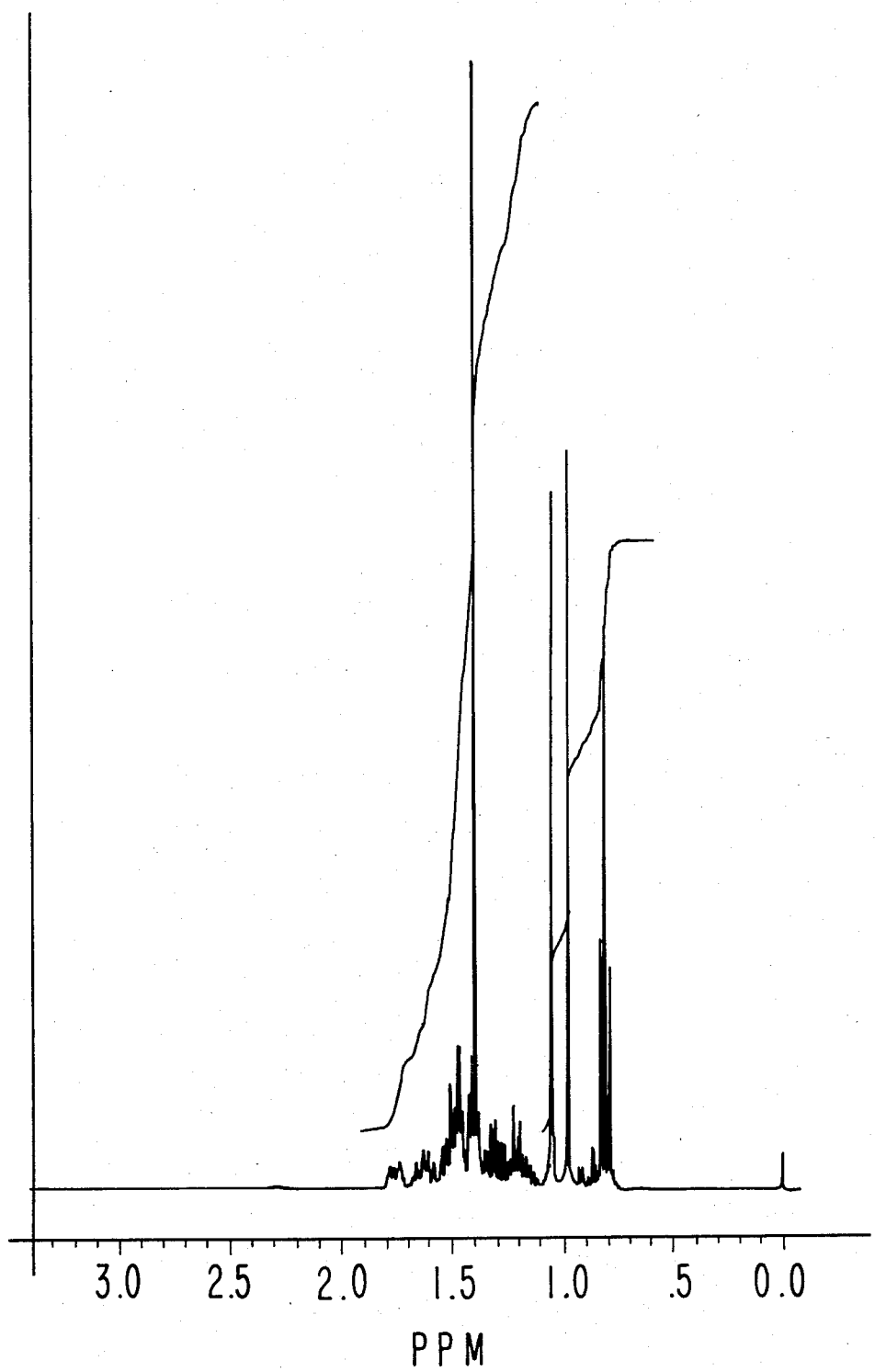

FIG. 3 is the NMR spectrum for bulked distillation fractions 1-3 of the distillation of the reaction product of Example I containing the compound having the structure:

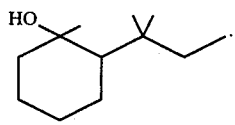

Figure 4:
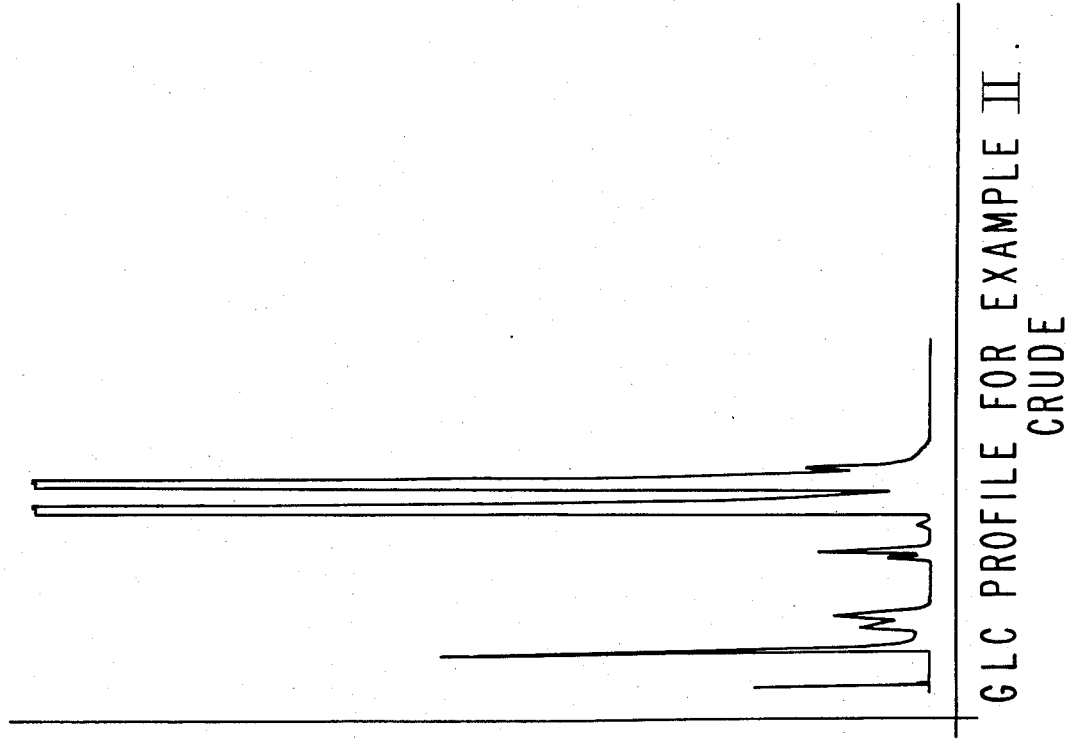

FIG. 4 is the GLC profile for the crude reaction product of Example II containing the compound having the structure:

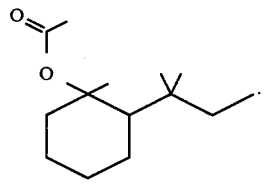

Figure 5:
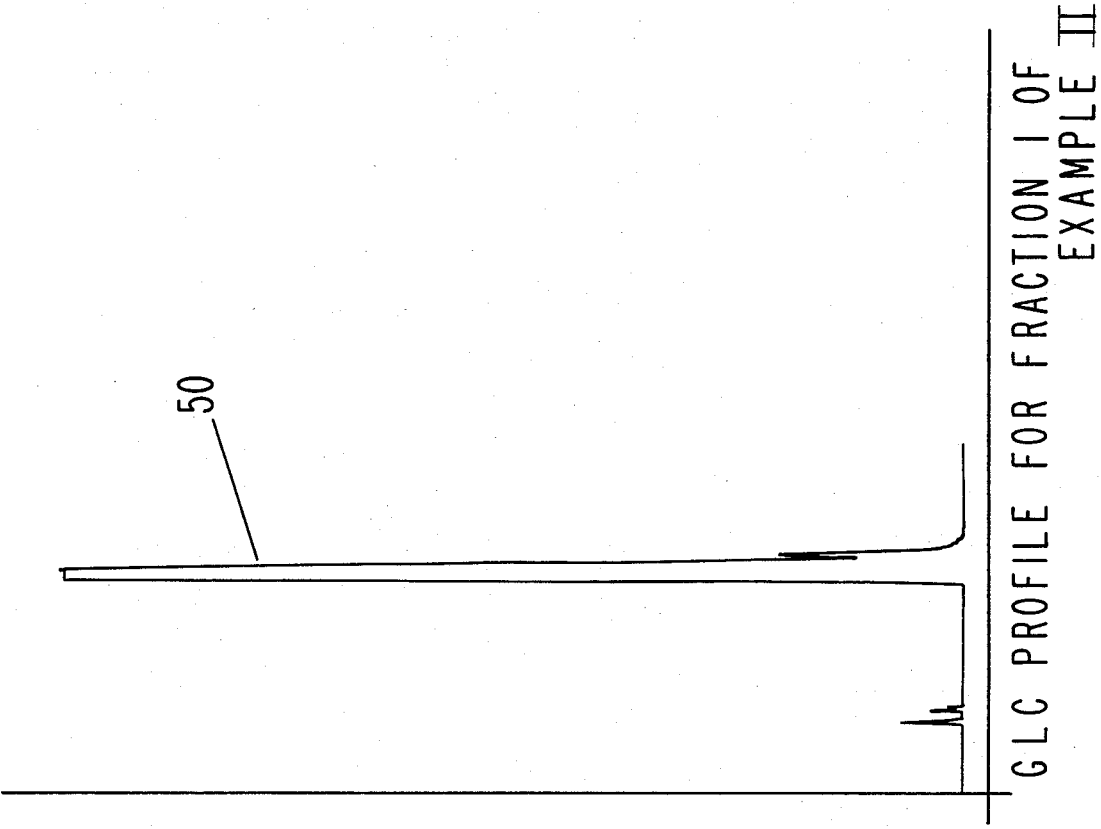

FIG. 5 is the GLC profile for fraction 1 of the distillation of the reaction product Example II containing the compound having the structure:

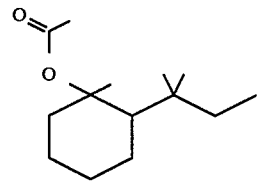

(Conditions: Carbowax column programmed at 150°-200° C. at 8° C. per minute).

FIG. 6 is the capillary GLC profile for bulked fractions 4-10 of the distillation of the reaction product of Example II containing the structure:

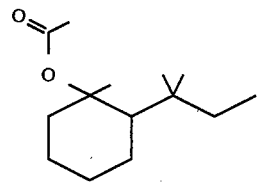

(Conditions: Methyl silicone/carbowax 20M column programmed from 75°-225° C. at 2° C. per minute).

FIG. 7 is the NMR spectrum for bulked distillation fractions 4-10 of the distillation of the reaction product of Example II containing the compound having the structure:

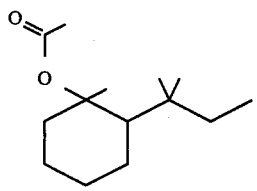

(Conditions: Field strength: 100 MHz; solvent: $CFCl_3$).

Figure 8:
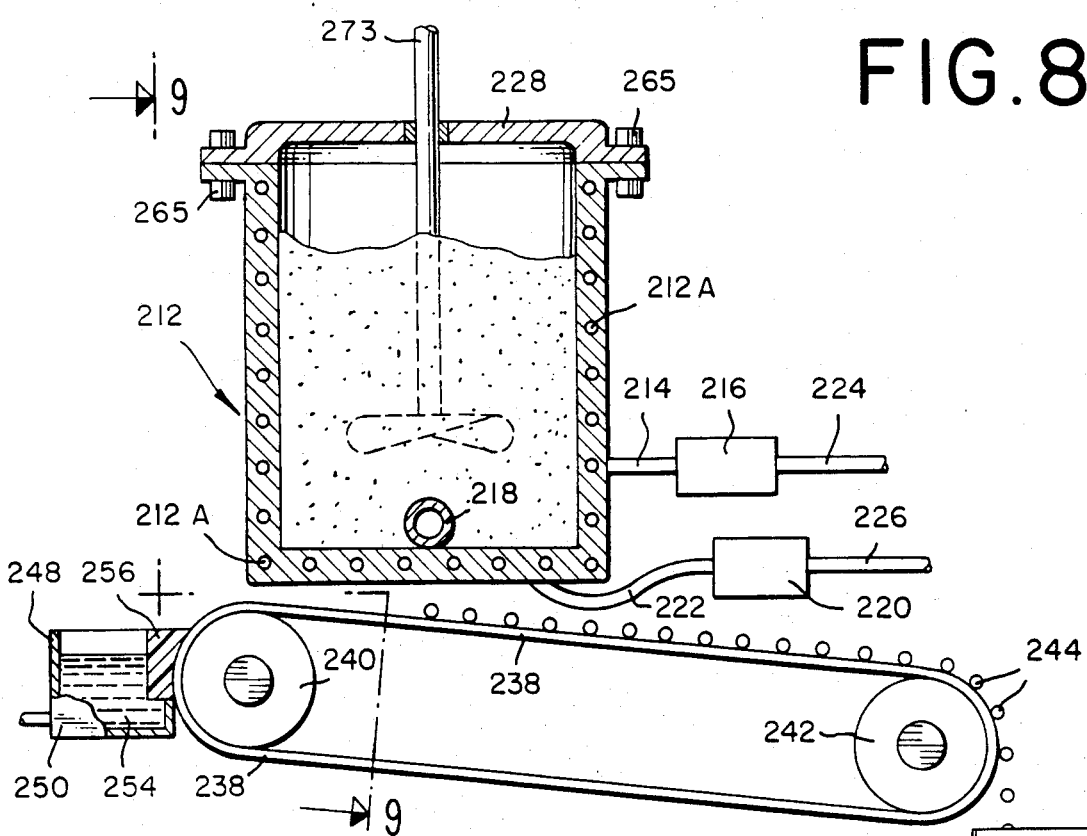

FIG. 8 is a partial side elevation and partial sectional view of an apparatus for forming polymer pellets containing at least one of the 1-methyl-2(2-methylbutyl)cyclohexanol derivatives of our invention.

Figure 9:
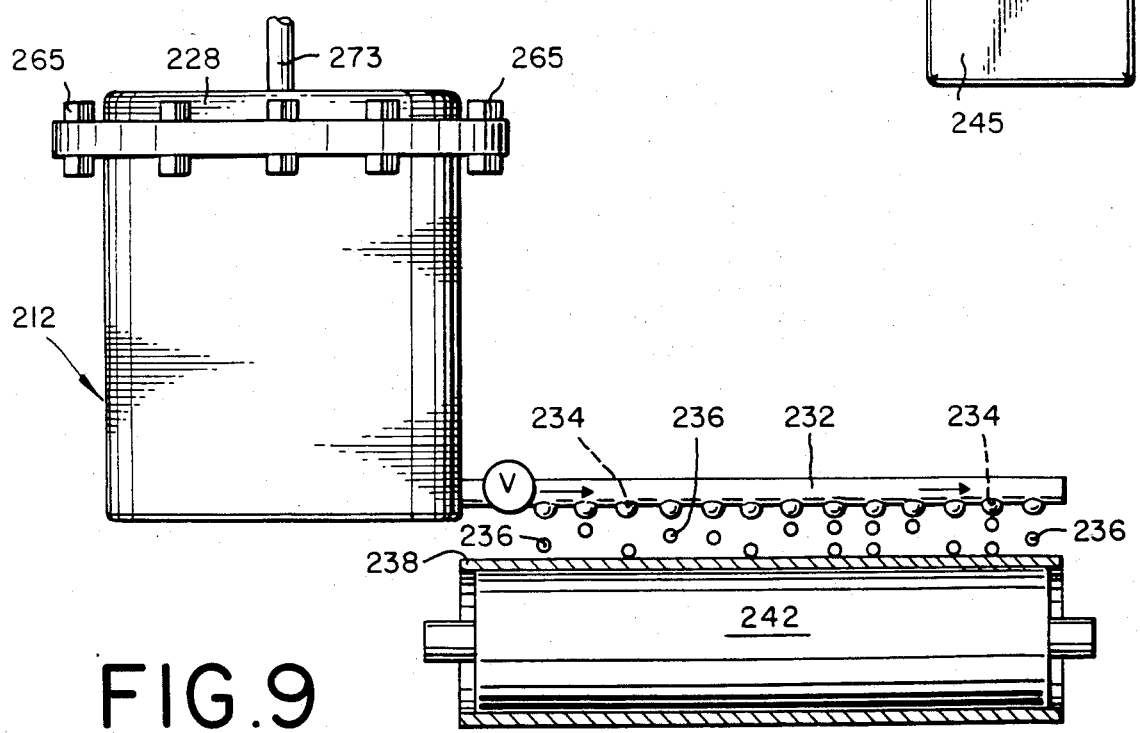

FIG. 9 is a section taken along the line 9—9 of FIG. 8.

DETAILED DESCRIPTION OF THE DRAWINGS

FIG. 2 is the GLC profile for bulked distillation fractions 1-3 of the distillation product of the reaction product of Example I containing the compound having the structure:

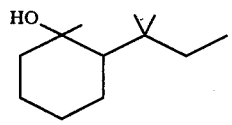

prepared according to Example I.

The peak indicated by reference numeral 20 is the peak for the compound having the structure:

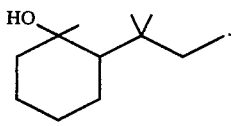

FIG. 5 is the GLC profile for fraction 1 of the distillation product of the reaction product of Example II containing the compound having the structure:

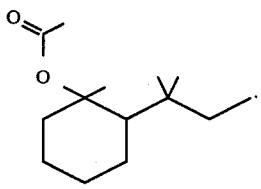

The peak indicated by reference numeral 50 is the peak for the compound having the structure:

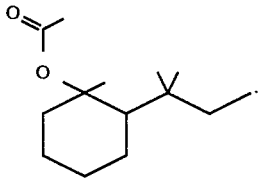

Referring to FIGS. 8 and 9 in particular, the apparatus used in producing polymeric fragrances containing the 1-methyl-2(2-methylbutyl)cyclohexanol derivatives of our invention comprises a device for forming scented polyolefin (for example) pellets, which comprises a vat or container 212 into which a mixture of polyolefins such as polyethylene and an aromatic substance or scented material is placed (in this case at least one of the 1-methyl-2(2-methylbutyl)cyclohexanol derivatives of our invention). The container is closed by an airtight lid 228 and clamped to the container by bolts 265. A stirrer 273 traverses the lid or cover 228 in airtight manner and is rotated in a suitable manner. A surrounding cylinder 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless odorless polymer (e.g., polyethylene) with viscosity ranging between 180 and 220 saybolt seconds and having a melting point in the range of 200°–280° F. The heater 212A is operated to maintain the upper portion of the container 212 within a temperature range of from 250°–350° F. The bottom portion of the container is heated by means of heating coils 212A heated through a control 220 connected thereto through a connecting wire 222 to maintain the lower portion of the container within a temperature range of from 250°–350° F.

Thus, polymer (e.g., polyethylene) is added to container 212 and is heated from 10–12 hours whereafter a scented aroma imparting material (at least one of the 1-methyl-2-(2-methylbutyl)cyclohexanol derivatives of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally about 5–30% by weight of the scented material (containing at least one of the 1-methyl-2(2-methylbutyl)cyclohexanol derivatives of our invention) are added to the polyolefin.

After the scent imparting material (e.g., a composition containing one of the 1-methyl-2(2-methylbutyl)cyclohexanol derivatives of our invention or one of the 1-methyl-2(2-methylbutyl)cyclohexanol derivatives of our invention taken alone) is added to the container 212, the mixture is stirred for a few minutes, for example, 5–15 minutes and maintained within the temperature range as indicated previously by heating coils 212A. The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter the valve "V" is opened permitting the mass to flow outwardly through conduit 218/232 having a multiplicity of orifices 234 adjacent to the lower side thereof. The outer end of the conduit 218/232 is closed so that the liquid polymer (e.g., polyolefin) and aroma imparting material (e.g., at least one of the 1-methyl-2(2-methylbutyl)cyclohexanol derivatives of our invention) will continuously drop through orifices 234 downwardly from conduit 232. During this time the temperature of the polymer (e.g., polyolefin) and scent imparting material (e.g., a mixture containing at least one of the 1-methyl-2(2-methylbutyl)cyclohexanol derivatives of our invention) is accurately controlled so that a temperature in the range of from about 210°–275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the 1-methyl-2(2-methylbutyl)cyclohexanol derivatives of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instantaneously and fall off the end of the conveyor 238 into a container 245 and utilized in processes as illustrated, infra.

A feature of this aspect of the process of our invention is the provision for moistening the conveyor belt 238 to insure rapid formation of the solid polymeric (e.g., polyolefin) scented pellets 244 without sticking to the belt. The belt 238 is advantageously fabricated of a material which will not normally stick to a melted plastic but a moistening means 248 insures a sufficiently cold temperature of the belt surface for adequate formation of the pellets 244. The adequate moistening means comprises a container 250 which is continuously fed with water 254 to maintain a level for moistening a sponge element 256 which bears against the exterior of the belt 238.

THE INVENTION

The invention comprises the novel products as well as novel processes according to which such products are manufactured, the specific embodiments of which are described hereinafter by way of example and in accordance with which it is now preferred to practice the invention.

Briefly, the present invention provides 1-methyl-2-(2-methylbutyl)cyclohexanol derivatives defined according to the structure:

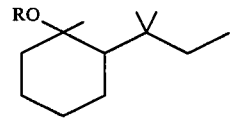

wherein R represents hydrogen, acetyl, MgCl, MgBr or lithium. Thus, the compounds having the structures:

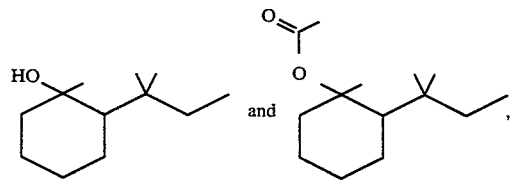

members of the aforementioned genus of the structure:

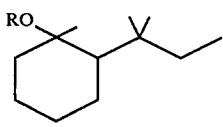

have utilities in augmenting or enhancing the aroma of consumable materials including perfume compositions, colognes and perfumed articles. The compounds having the structures:

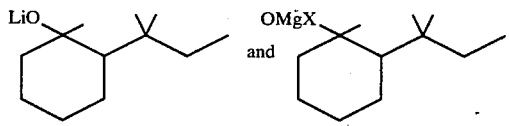

(wherein X is Cl or Br) of the aforementioned genus having the structure:

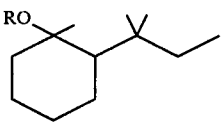

are useful as intermediates in preparing the compounds having the structures:

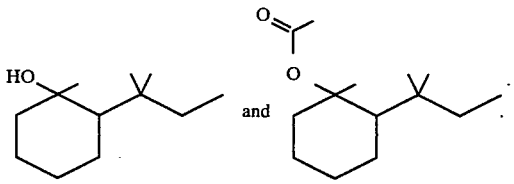

The compounds defined according to the structure:

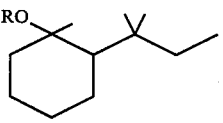

wherein R represents hydrogen, acetyl, MgCl, MgBr or lithium are novel compounds.

The compounds defined according to the structures:

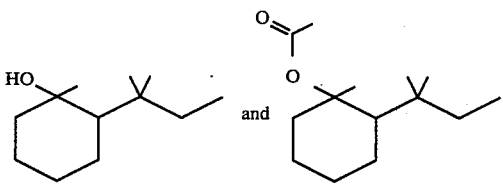

of our invention augment or enhance the aroma of perfume compositions, colognes and perfumed articles by augmenting or enhancing earthy, minty, fresh, camphoraceous, woody, ambery and herbaceous aromas with floral and cedarwood undertones and cooling effects.

The compounds of our invention having the structure:

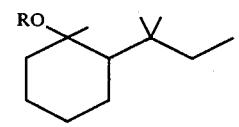

may be prepared by first reacting the compound having the structure:

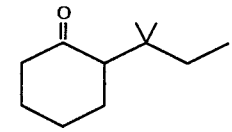

with methyl lithium or a methyl magnesium halide (e.g., methyl magnesium bromide or methyl magnesium chloride) under anhydrous conditions in order to produce one of the organometallic compounds having a structure:

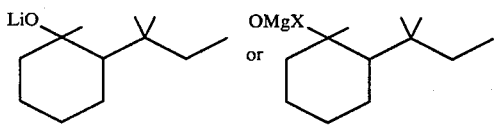

(wherein X is Cl or Br).
according to the reaction:

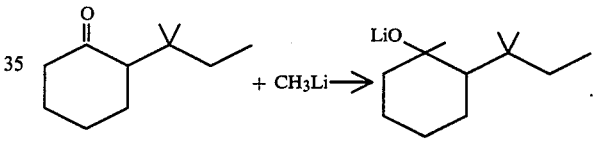

or the reaction:

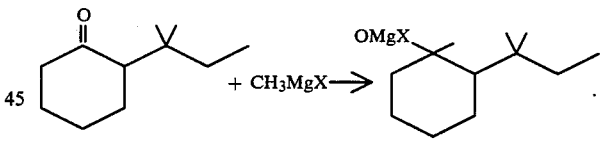

The mole ratio of the methyl magnesium halide or the methyl lithium: compound having the structure:

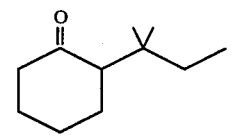

is approximately 1:1 with the compound having the structure:

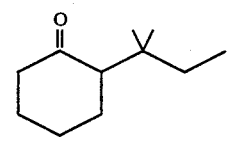

being in slight excess.
The compound having the structure:

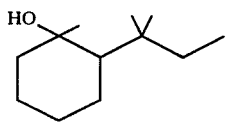

is produced by reacting one of the thus-formed organo-metallic compounds having one of the structures:

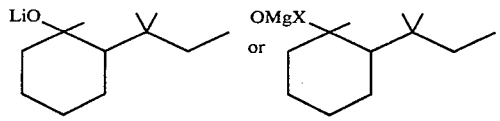

with an acid in the presence of water or an acid salt in the presence of water according to one of the reactions:

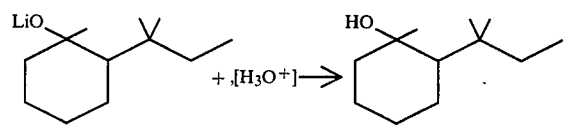

or

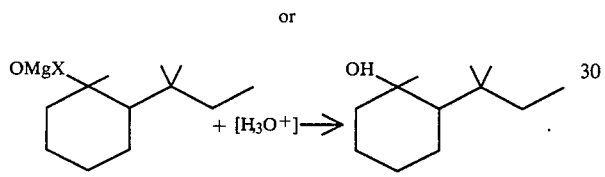

The resulting compound having the structure:

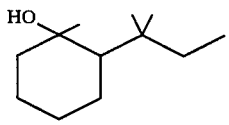

may be used "as is" for its organoleptic properties after carrying out a fractional distillation on the reaction product and bulking the odor-acceptable fractions. On the other hand, the compound having the structure:

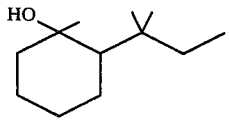

may be further reacted by means of esterification with acetic anhydride in order to produce the compound having the structure:

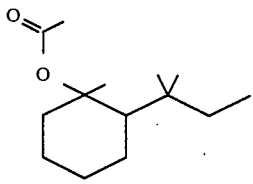

according to the reaction:

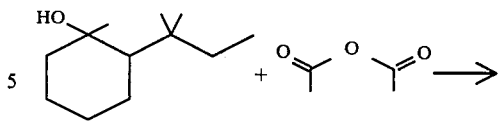

The process embodied by the reaction:

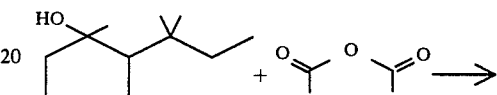

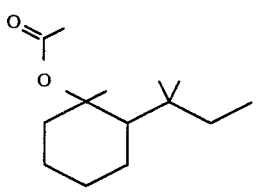

is a novel process when the reaction is carried out in the presence of methane sulfonic acid, $CH_3HSO_3$ at a temperature in the range of $-5°$ C. up to $+5°$ C. with a preferred reaction temperature of $-2°$ C. up to $0°$ C. At the end of the reaction the reaction mass is distilled at mixture with calcium carbonate. The mole ratio of compound having the structure:

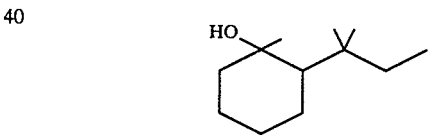

to acetic anhydride may vary from about 1:1 to about 1.5:1. The amount of methane sulfonic acid in the reaction mass may vary from about 0.8% by weight of the reaction mass up to about 1.2% by weight of the reaction mass. The time of reaction may vary from about 10 up to about 40 hours with a preferred reaction time of 15–20 hours.

Examples of the 1-methyl-2(2-methylbutyl)cyclohexanol derivatives of our invention and their organoleptic properties are set forth in the following Table I:

TABLE I

| 1-METHYL-2(2-METHYL-BUTYL) CYCLOHEXANOL DERIVATIVES OF OUR INVENTION | PERFUMERY PROPERTY |
|---|---|
| Compound having the structure: <br> HO- <br> bulked fractions 2 and 3 prepared according to Example I, | An earthy, minty, fresh, camphoraceous aroma with floral undertones and a cooling effect. |

TABLE I-continued

| 1-METHYL-2(2-METHYL-BUTYL) CYCLOHEXANOL DERIVATIVES OF OUR INVENTION infra | PERFUMERY PROPERTY |
|---|---|
| Compound having the structure: 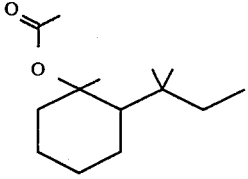  bulked fractions 4-10 of Example II, infra | A woody, ambery, minty and herbaceous aroma with cedarwood undertones. |

The 1-methyl-2(2-methylbutyl)cyclohexanol derivatives of our invention and one or more auxilliary perfumery ingredients including, for example, alcohols other than the 1-methyl-2(2-methylbutyl)cyclohexanol derivatives of our invention, aldehydes, ketones, terpinic hydrocarbons, nitriles, esters other than the 1-methyl-2(2-methylbutyl)cyclohexanol derivatives of our invention, amines, natural synthetic oils and synthetic essential oils may be admixed so that the combined odors of the individual components produce a pleasant and desired fragrance particularly and preferably in the earthy, minty, ambery, herbaceous and cedarwood fragrances.

Such perfume compositions usually contain (a) the main note or the "bouquet" or foundation stone of the composition; (b) modifiers which round off and accompany the main note; (c) fixatives which include odorous compositions which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the over-all sensory effect of the perfume composition will be at least the sum total of the effects of each of the ingredients. Thus, the 1-methyl-2(2-methylbutyl)cyclohexanol derivatives of our invention can be used to alter, modify or enhance the aroma characteristics of a perfume composition, for example, by utilizing or moderating the olfactory reaction contributed by another ingredient in the composition.

The amount of the 1-methyl-2(2-methylbutyl)cyclohexanol derivatives of our invention which will be effective in perfume compositions as well as in perfumed articles and colognes depends on many factors, including the other ingredients, their amounts and the effects which are desired. It has been found that perfume compositions containing as little as 0.01% of the 1-methyl-2(2-methylbutyl)cyclohexanol derivatives of our invention or even less (e.g., 0.005%) can be used to impart, augment or enhance earthy, minty, fresh, camphoraceous, woody, ambery and herbaceous aromas with floral and cedarwood undertones and cooling effects to soaps, cosmetics or other products. The amount employed can range up to 70% of the fragrance components and will depend on consideration of cost, nature of the end product and the particular fragrance sought.

The 1-methyl-2(2-methylbutyl)cyclohexanol derivatives of our invention are useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders and the like. When used as (an) olfactory component(s) in perfumed articles as little as 0.1% of the 1-methyl-2(2-methylbutyl)cyclohexanol derivatives of our invention or composition containing a high proportion of the 1-methyl-2(2-methylbutyl)cyclohexanol derivatives of our invention will suffice to impart, augment or enhance intense long lasting earthy, minty, fresh, camphoraceous, woody, ambery and herbaceous aromas with floral and cedarwood undertones and cooling effects.

The range of 1-methyl-2(2-methylbutyl)cyclohexanol derivatives of our invention useful in perfumed articles including solid or liquid anionic, cationic, nonionic or zwitterionic detergents, soaps, space odorants and deodorants, bath preparations, such as creams, deodorants, hand lotions and sun screens; powders, such as talcs, dusting powders, face powders and the like and perfumed polymers may vary from as little as 0.1% to as much as 5% of the 1-methyl-2(2-methylbutyl)cyclohexanol derivatives of our invention.

In addition, the perfume composition or fragrance composition of our invention can contain a vehicle or carrier for the 1-methyl-2(2-methylbutyl)cyclohexanol derivatives of our invention. The vehicle can be a liquid, such as an alcohol, such as ethyl alcohol, a non-toxic glycol, such as propylene glycol or the like. The carrier can also be an absorbent solid, such as gum (i.e., gum arabic, guar gum, xanthan gum or the like) or components for encapsulating the composition (such as gelatin when encapsulation is carried out by means of coacervation or such as a urea formaldehyde prepolymer when encapsulation is carried out by forming a polymeric wall around a liquid perfume center).

The following Examples I and II serve to illustrate methods for preparation of the 1-methyl-2(2-methylbutyl)cyclohexanol derivatives of our invention. The examples following Examples II, that is Examples III, et seq, show methods for utilizing the organoleptic properties of the 1-methyl-2(2-methylbutyl)cyclohexanol derivatives of our invention. It will be understood that these examples are illustrative and the invention is to be considered as restricted thereto only as indicated in the appended claims.

EXAMPLE I

PREPARATION OF 1-METHYL-2-TERTIARY AMYL CYCLOHEXANOL

Reactions:

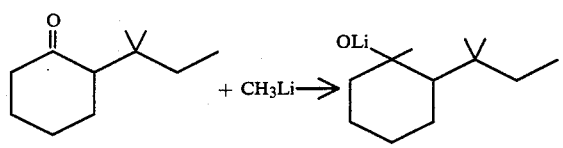

and

-continued

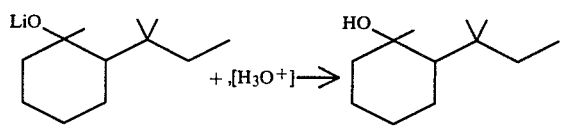

Into a 12 liter reaction flask equipped with stirrer, thermo-watch, dropping funnel, cooling bath and nitrogen inlet apparatus is placed 6 moles of methyl lithium dissolved in diethyl ether. The methyl lithium solution is cooled to −10° C. using a dry-ice/acetone mixture. With stirring over a period of 0.5 hours, 600 grams (3.57 moles) of the compound having the structure:

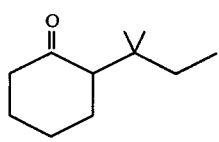

is added to the reaction mass. The resulting mixture is stirred for a period of two hours. At the end of the two hour period, the reaction mass shows no ketone and contains as a reaction product the compound having the structure:

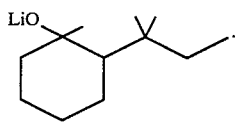

The reaction mixture is then admixed with an aqueous solution of ammonium chloride (mole ratio ammonium chloride: compound having the structure:

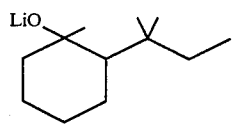

being 3:1).

The purpose of the aqueous ammonium chloride is to hydrolyze the compound having the structure:

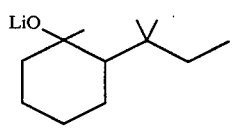

in order to form the compound having the structure:

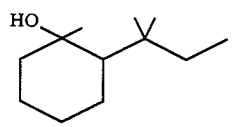

according to the reaction:

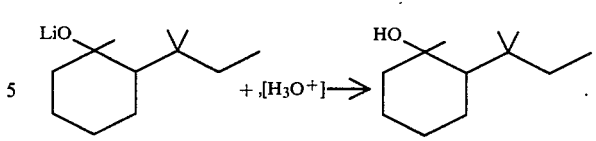

The organic layer (containing the diethyl ether) is separated from the aqueous phase and the organic phase is washed with one 200 ml portion of saturated sodium bicarbonate. The ether extract is then concentrated and distilled yielding the following fractions:

| FRACTION NO. | VAPOR TEMP (°C.) | LIQUID TEMP. (°C.) | VACUUM PRESSURE mm/Hg |
|---|---|---|---|
| 1 | 67/78 | 105/113 | 2.4 |
| 2 | 87 | 113 | 2.3 |
| 3 | 85 | 115 | 2.3 |

Figure 1:
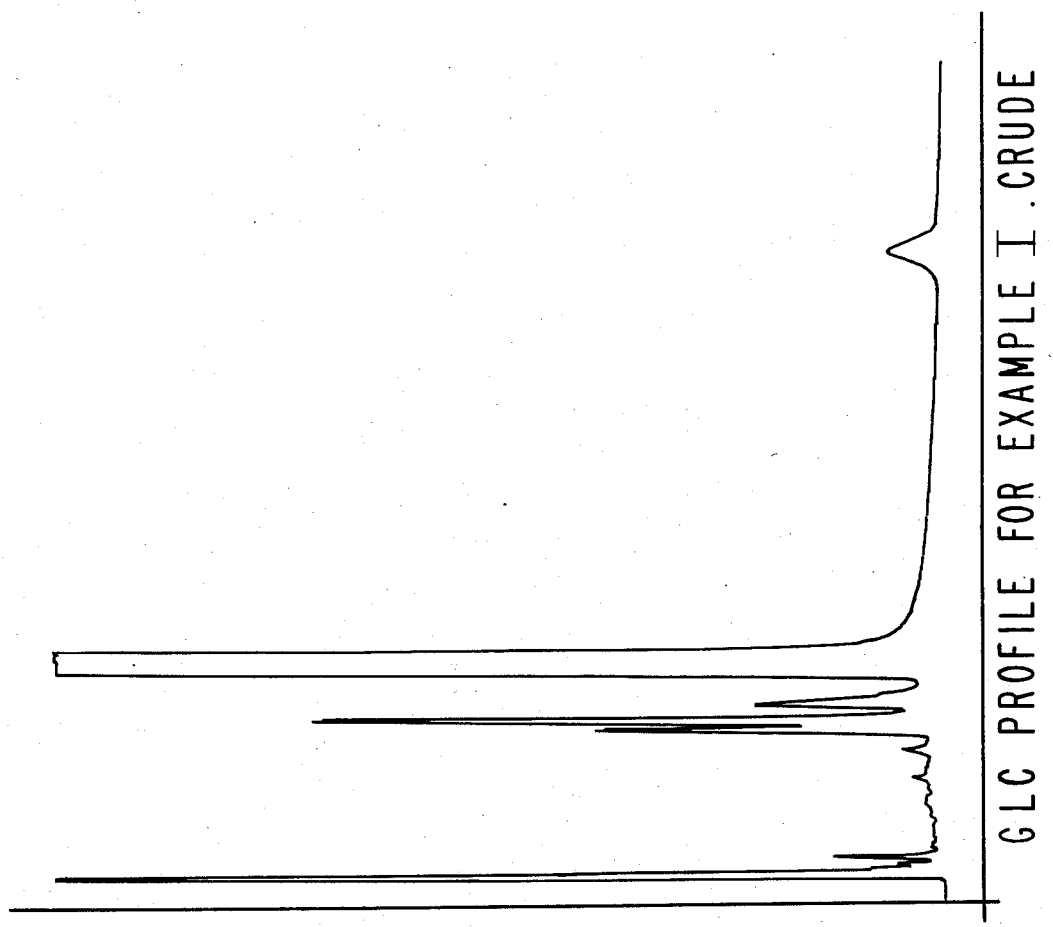
FIG. 1 is the GLC profile for the crude reaction product of Example I containing the compound having the structure.

FIG. 1 is the GLC profile for the crude reaction product containing the compound having the structure:

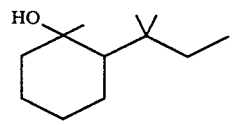

(Conditions: Carbowax column programmed at 150°–200° C. at 8° C. per minute).

FIG. 2 is the GLC profile for bulked distillation fractions 1–3 of the foregoing distillation containing the compound having the structure:

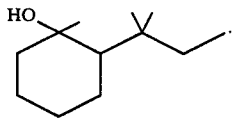

The peak indicated by reference numeral 20 is the peak for the compound having the structure:

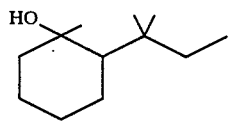

FIG. 3 is the NMR spectrum for bulked fraction 1–3 of the foregoing distillation for the compound having the structure:

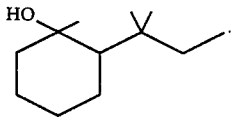

The compound having the structure:

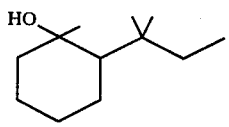

has an earthy, minty, fresh, camphoraceous aroma with floral undertones and a cooling effect.

EXAMPLE II

PREPARATION OF 1-METHYL-2-t-AMYL CYCLOHEXYL ACETATE

Reaction:

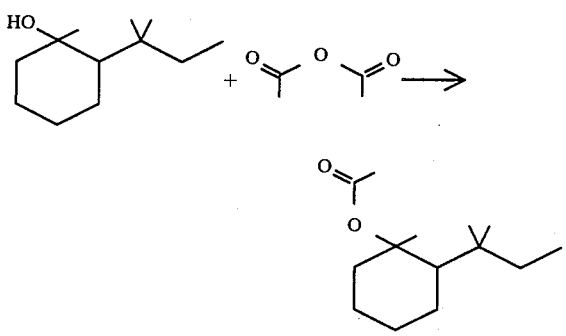

Into a 3 liter three neck round bottom flask equipped with stirrer, addition funnel and laboratory jack, with stirring is added a mixture containing 427 grams (4.18 moles) of acetic anhydride and 7 grams of methane sulfonic acid. With stirring over a period of 20 minutes is added 700 grams (3.8 moles) of the compound having the structure:

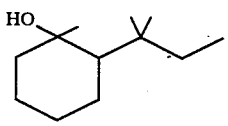

prepared according to Example I, bulked fractions 1-3. The reaction mass is cooled to −2° C. and maintained at 0-minus 2° C. for a period of 15 hours. At the end of the 15 hour period the reaction mass shows 10% starting material remaining having the structure:

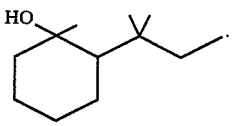

The reaction mass is then stirred for an additional 12 hours at the end of which time the reaction mass shows no starting material having the structure:

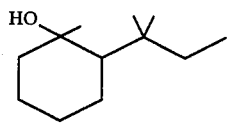

remaining.

The reaction mass is then "worked up" by adding 500 grams of ice thereto. The aqueous phase is separated from the organic phase and the organic phase is washed with two 250 ml portions of ice water and then made basic with saturated sodium bicarbonate and then filtered. The resulting product is dried over anhydrous magnesium sulphate and distilled on a 1'×12" stone packed silver column yielding the following fractions:

| FRACTION NO. | VAPOR TEMP (°C.) | LIQUID TEMP. (°C.) | VACUUM PRESSURE mm/Hg |
|---|---|---|---|
| 1 | 40/65 | 95/105 | 2.15 |
| 2 | 79 | 110 | 2.15 |
| 3 | 87 | 112 | 2.15 |

Fractions 2 and 3 are bulked and the bulked fractions are then distilled on a 1"×6" stone packed column yielding the following fractions:

| FRACTION NO. | VAPOR TEMP (°C.) | LIQUID TEMP. (°C.) | VACUUM PRESSURE mm/Hg | WEIGHT OF FRACTION |
|---|---|---|---|---|
| 1 | 88/91 | 114/117 | 2.2 | 22.0 |
| 2 | 90 | 122 | 1.0 | 28.9 |
| 3 | 90 | 120 | 2.1 | 44.4 |
| 4 | 90 | 120 | 2.0 | 45.4 |
| 5 | 91 | 120 | 0.8 | 57.3 |
| 6 | 91 | 121 | 1.8 | 50.1 |
| 7 | 95 | 121 | 0.9 | 45.1 |
| 8 | 97 | 122 |  | 46.9 |
| 9 | 95 | 122 | 0.9 | 45.3 |
| 10 | 101 | 123 | 3.0 | 40.4 |
| 11 | 94 | 124 | 3.0 | 45.8 |
| 12 | 100 | 130 | 3.0 | 22.3 |
| 13 | 97 | 165 | 3.0 | 8.2 |

FIG. 4 is the GLC profile for the crude reaction product prior to distillation.

FIG. 5 is the GLC profile for fraction 1 of the foregoing distillation (second distillation) (Conditions: Carbowax column programmed at 150°-200° C. at 8° C. per minute).

The peak indicated by reference numeral 50 is the peak for the compound having the structure:

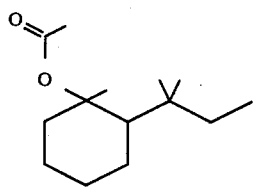

FIG. 6 is the capillary GLC profile for bulked fractions 4-10 of the foregoing distillation (Conditions: Methyl silicone/carbowax 20M fused silica capillary column programmed at 75°-225° C. at 2° C. per minute).

FIG. 7 is the NMR spectrum for bulked fractions 4-10 of the foregoing distillation containing the compound having the structure:

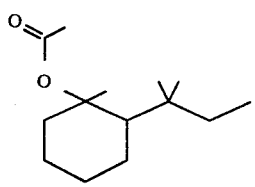

(Conditions: Field strength: 100 MHz; solvent: CFCl₃).

The compound having the structure:

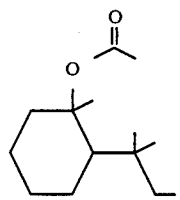

(bulked fractions 4–10) has a woody, ambery, minty and herbaceous aroma with cedarwood and undertones. The capillary GC product containing 100% pure compound having the structure:

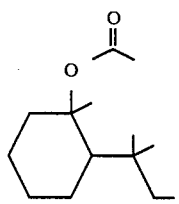

has a woody, ambery, ambergris-like, cedarwood and slightly musky aroma nuance.

When the compound having the structure:

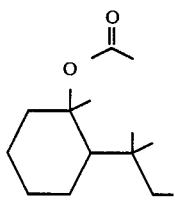

is compared to the compound having the structure:

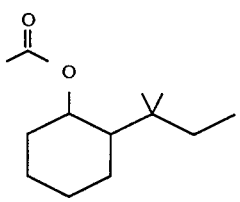

of the prior art (reference: Arctander monograph 167 cited, supra), the compound having the structure:

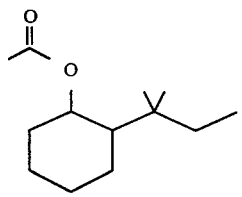

has a very sweet, woody, balsamic, green, fruity (raspberry), and piney (fir balsam absolute-like) aroma profile as opposed to the woody, ambery, ambergris-like, cedarwood and musky aroma profile of the compound having the structure:

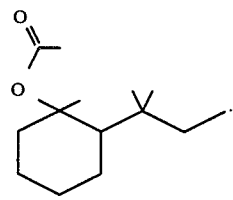

EXAMPLE III

Perfume compositions are prepared with the following ingredients:

| INGREDIENTS | III(A) PARTS BY WEIGHT | III(B) PARTS BY WEIGHT | III(C) PARTS BY WEIGHT |
|---|---|---|---|
| Vetivert oil | 40 | 40 | 40 |
| Sandalwood oil | 100 | 100 | 100 |
| Rose geranium oil | 200 | 200 | 200 |
| Musk extrace (3% diethyl phthalate) | 25 | 25 | 25 |
| Civet extrace (3% diethyl phthalate) | 25 | 25 | 25 |
| Benzyl-isoeugenol | 100 | 100 | 100 |
| Coumarin | 100 | 100 | 100 |
| Heliotropin | 50 | 50 | 50 |
| Bois de rose oil | 200 | 200 | 200 |
| Benzoin resin | 100 | 100 | 100 |
| Compound having the structure: HO- | 30 | 0 | 0 |
| Compound having the structure: | 0 | 30 | 0 |
| 50:50 mixture of compounds having the structures: HO- and | 0 | 0 | 30 |

| INGREDIENTS | III(A) PARTS BY WEIGHT | III(B) PARTS BY WEIGHT | III(C) PARTS BY WEIGHT |
|---|---|---|---|
| 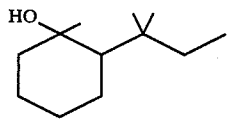 | | | |

The perfume composition of Example III(A) has an excellent musk, amber and woody aroma profile with earthy, minty, fresh and camphoraceous undertones and a cooling effect caused by the use of the compound having the structure:

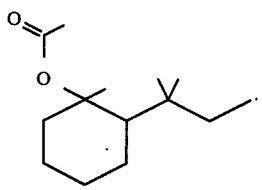

(bulked fractions 2 and 3 of Example I).

The perfume composition of Example III(B) has a musk, amber and woody aroma profile with woody, minty, herbaceous and cedarwood undertones, the woody, minty, herbaceous and cedarwood undertones and intensified amber quality being caused by the use of the compound having the structure:

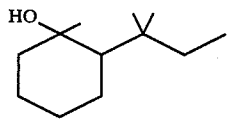

The perfume composition of Example III(C) has a musk, amber and woody aroma with minty, fresh, camphoraceous, floral, herbaceous and cedarwood undertones, the undertones being caused by the use of the compounds having the structures:

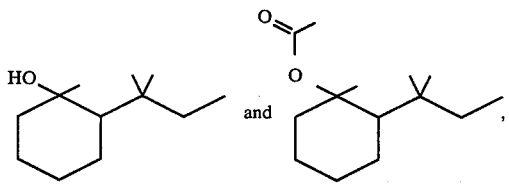

the greater intensity of amber quality and woody quality being caused by the use of the compound having the structure:

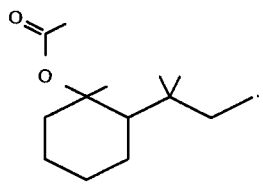

EXAMPLE IV

PREPARATION OF A COSMETIC POWDER COMPOSITION

A cosmetic powder is prepared by mixing in a ball mill, 100 grams of talcum powder with 0.25 grams of one of the perfumery substances set forth in Table II below. Each of the cosmetic powders has an excellent intense aroma as set forth in Table II below:

TABLE II

| PERFUME SUBSTANCE | PERFUMERY EVALUATION |
|---|---|
| Compound having the structure:<br><br>(bulked fractions 2 and 3 of Example I) | An earthy, minty, fresh, camphoraceous aroma with floral undertones and a cooling effect. |
| Compound having the structure:<br><br>(bulked fractions 4–10 of Example II) | A woody, ambery, minty and herbaceous aroma with cedarwood undertones. |
| Perfume composition of Example III(A) | An excellent musk, amber and woody aroma profile with earthy, minty, fresh and camphoraceous undertones and a cooling effect. |
| Perfume composition of Example III(B) | A musk, amber and woody aroma profile with woody, minty, herbaceous and cedarwood undertones. |
| Perfume composition of Example III(C) | A musk, amber and woody aroma with minty, fresh, camphoraceous, floral, herbaceous and cedarwood undertones. |

EXAMPLE V

PERFUMED LIQUID DETERGENT

Concentrated liquid detergents with aromas as set forth in Table II of Example IV (which detergents are prepared from Lysine salt of n-dodecyl benzene sulfonic acid as more specifically described in U.S. Pat. No. 3,948,818 issued on Apr. 6, 1976, the specification of which is incorporated by reference herein), are prepared containing each of the substances set forth in Table II of Example IV, supra. They are prepared by adding and homogeneously mixing the appropriate quantity of perfumery substances as set forth in Table II of Example IV in the liquid detergent. The detergents all possess aromas as set forth in Table II of Example IV, the intensity increasing with greater concentrations of perfumery substance of Table II of Example IV, supra.

EXAMPLE VI

PREPARATION OF A COLOGNE AND HANDKERCHIEF PERFUME

The perfume substances of Table II of Example IV, supra, are incorporated into colognes at concentrations of 1.5%, 2.0%, 2.5%, 3.0% and 4.0% in 80%, 85% and 90% aqueous ethanols; and into handkerchief perfume compositions at concentrations of 10%, 15%, 20%, 25%, and 30% (in 85%, 90% and 95% aqueous ethanols). Distinct and definitive aromas as set forth in Table II of Example IV are imparted to the cologne and to the handkerchief perfume compositions.

EXAMPLE VII

PREPARATION OF A DETERGENT COMPOSITION

A total of 100 grams of a detergent powder (a nonionic detergent powder containing a proteo lytic enzyme prepared according to Example I of Canadian Pat. No. 985,190 issued on Mar. 9, 1976, the disclosure of which is incorporated by reference herein), is mixed with 0.15 grams of each of the substances set forth in Table II of Example IV, supra, until substantially homogeneous compositions are obtained. These compositions have excellent aromas as set forth in Table II of Example IV.

EXAMPLE VIII

PREPARATION OF SOAP

Each of the perfumery substances of Table II of Example IV are incorporated into soap (LVU-1) at 0.1% by weight of each substance. After two weeks in the oven at 90° F. each of the soaps showed no visual effect from the heat. Each of the soaps manifested an excellent aroma as set forth in Table II of Example IV, supra.

EXAMPLE IX

PREPARATION OF SOAP COMPOSITION

One hundred grams of soap chips (IVORY ®, registered trademark of the Procter & Gamble Co. of Cincinnati, Ohio) are mixed individually with one gram each of the perfumery substances of Table II of Example IV, supra, until a homogeneous composition is obtained. The homogeneous composition is then treated under three atmospheres pressure at 180° C. for a period of three hours and the resulting liquid is placed into a soap mold. The resulting soap cakes, on cooling, manifest excellent aromas as set forth in Table II of Example IV, supra.

EXAMPLE X

PREPARATION OF A SOLID DETERGENT COMPOSITION

A detergent is prepared from the following ingredients according to Example I of Canadian Pat. No. 1,007,948 the specification for which is incorporated by reference herein):

| INGREDIENTS | PARTS BY WEIGHT |
| --- | --- |
| "Neodol 45-11" (a $C_{14}$-$C_{15}$ alcohol ethoxylated with 11 moles of ethylene oxide | 12 |
| Sodium carbonate | 55 |
| Sodium citrate | 20 |
| Sodium sulfate, water | q.s. |

| INGREDIENTS | PARTS BY WEIGHT |
| --- | --- |
| brighteners | |

This detergent is a "phosphate-free" detergent. A total of 100 grams of this detergent is admixed separately with 0.15 grams of each of the perfume substances of Table II of Example IV, supra. The detergent samples each have excellent aromas as set forth in Table II of Example IV, supra.

EXAMPLE XI

Utilizing the procedure of Example I at column 15 for U.S. Pat. No. 3,632,396, the specification for which is incorporated by reference herein, a non-woven cloth substrate useful as a dryer-added fabric softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.);
   57 percent $C_{20-22}$ HAPS
   22 percent isopropyl alcohol
   20 percent antistatic agent
   1 percent of one of the perfume substances of Table II of Example IV, supra.

A fabric softening composition prepared as set forth above having the above aroma characteristics as set forth in Table II of Example IV, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table II of Example IV is imparted in a pleasant manner to the headspace in the dryer on operation thereof, using said dryer-added fabric softening non-woven fabric.

What is claimed is:

1. A 1-methyl-2(2-methylbutyl)cyclohexanol derivative defined according to the structure:

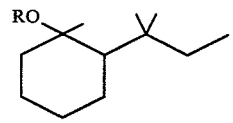

wherein R represents lithium, MgCl, MgBr, hydrogen or acetyl.

2. The compound of claim 1 wherein R is lithium.
3. The compound of claim 1 wherein R is hydrogen.
4. The compound of claim 1 wherein R is acetyl.
5. A process for augmenting or enhancing the aroma of a consumable material selected from the group consisting of perfume compositions, colognes and perfumed articles comprising the step of adding to said consumable material an aroma augmenting or enhancing quantity of at least one compound defined according to the structure:

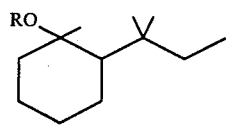

wherein R represents hydrogen or acetyl.

6. The process of claim 5 wherein the compound added to the consumable material has the structure:

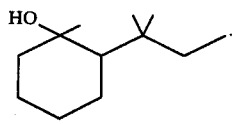

7. The process of claim 5 wherein the compound added to the consumable material has the structure:

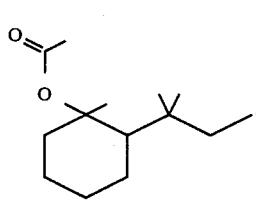

8. The process of claim 5 wherein the consumable material is a perfume composition or cologne.

9. The process of claim 5 wherein the consumable material is a perfumed article and the perfumed article is a perfumed polymer.

10. The process of claim 5 wherein the consumable material is a perfumed article and the perfumed article is a solid or liquid anionic, cationic, nonionic or zwitterionic detergent.

11. The process of claim 5 wherein the consumable material is a perfumed article and the perfumed article is a fabric softener composition or fabric softener article.

12. The composition of claim 1 in substantially pure form.

13. The compound of claim 1 wherein R is MgCl or MgBr.

14. A process for preparing the compound having the structure:

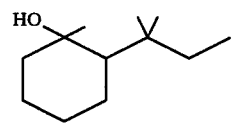

comprising the step of reacting the compound having the structure:

with acetic anhydride according to the reaction:

in the presence of CH$_3$HSO$_3$ at a temperature in the range of $-5°$ C. up to $+5°$ C., with the mole ratio of compound having the structure:

to acetic anhydride varying between about 1:1 up to about 1.5:1, and with the amount of methane sulfonic acid in the reaction mass varying from about 0.8% by weight of the reaction mass up to about 1.2% by weight of the reaction mass, and with the time of reaction varying from about 10 up to about 40 hours.

* * * * *